United States Patent
Yamaguchi et al.

(10) Patent No.: US 8,484,155 B2
(45) Date of Patent: Jul. 9, 2013

(54) HAIR EVALUATION METHOD AND SYSTEM

(75) Inventors: Masakazu Yamaguchi, Tokyo (JP); Takashi Ito, Tokyo (JP); Shinobu Nagase, Tokyo (JP); Chihiro Saegusa, Tokyo (JP)

(73) Assignee: Kao Corporation, Tokyo (JP)

(*) Notice: Subject to any disclaimer, the term of this patent is extended or adjusted under 35 U.S.C. 154(b) by 720 days.

(21) Appl. No.: 12/524,974

(22) PCT Filed: Jan. 30, 2008

(86) PCT No.: PCT/JP2008/051416
§ 371 (c)(1), (2), (4) Date: Jul. 29, 2009

(87) PCT Pub. No.: WO2008/093735
PCT Pub. Date: Aug. 7, 2008

(65) Prior Publication Data
US 2010/0106679 A1    Apr. 29, 2010

(30) Foreign Application Priority Data
Jan. 30, 2007 (JP) .................................. 2007-020211

(51) Int. Cl.
*G06N 7/04* (2006.01)
*A45D 44/00* (2006.01)

(52) U.S. Cl.
CPC ...................................... *A45D 44/00* (2013.01)
USPC ............................................ 706/54; 132/333

(58) Field of Classification Search
CPC ........................................................ A45D 44/00
USPC ............................................ 706/54; 132/333
See application file for complete search history.

(56) References Cited

FOREIGN PATENT DOCUMENTS

| JP | 57-173755 | 10/1982 |
|----|-----------|---------|
| JP | 5-215681 | 8/1993 |
| JP | 7-306200 | 11/1995 |
| JP | 8-29258 | 2/1996 |
| JP | 2000-206043 | 7/2000 |
| JP | 2000-206044 | 7/2000 |
| JP | 2000-287953 | 10/2000 |
| JP | 2005-348905 | * 12/2005 |

OTHER PUBLICATIONS

"Trace Elements in Hair, as Related to Exposure in Metropolitan New York", John P. Creason, Thomas A. Hinners, Joseph E. Bumgarner, Cecil Pinkerton, Clinical Chemistry, Apr. 1975, vol. 21 No. 4, pp. 603-612.*

(Continued)

*Primary Examiner* — Kakali Chaki
*Assistant Examiner* — Mai T Tran
(74) *Attorney, Agent, or Firm* — Oblon, Spivak, McClelland, Maier & Neustadt, L.L.P.

(57) ABSTRACT

A relation equation between wave information on unpermed hair strands and evaluation values of appearance of whole hair selected from among gloss of the whole hair, order of alignment of the hair strands, and frizziness of the hair strand is acquired from a plurality of subjects. Based on the relation equation, the appearance of whole hair of an arbitrary subject is evaluated from wave information on a hair strand of the arbitrary subject. This allows an objective evaluation of the gloss of whole hair, the order of alignment of hair strands, or the frizziness of the hair strand by a simple technique, and also allows an objective evaluation corresponding to cosmetic specialists' evaluations in terms of equivalent age.

6 Claims, 9 Drawing Sheets

OTHER PUBLICATIONS

Communication issued on Sep. 26, 2011 in the corresponding European Application No. 08 704 179.4.

Yoshio Kajiura, et al., "Structural analysis of curly human hair strands by scanning micro-beam SAXS", Journal of The Japanese Society for Synchrotron Radiation Research, vol. 19, No. 6, pp. 371-377, 2006. (English translation only).

Hiroyuki Taguchi, "Development of Method for Evaluating Hair Form and its Application", Legal Medicine, vol. 59, No. 1, 69, 2006. (English translation only).

C.R. Robbins., "Chemical and Physical Behavior of Human Hair", Springer-Verlag, pp. 77-79, 2002.

Naoki Suzuki et al., "The Development of the Apparatus for Evaluating Hair Luster", Journal of Society of Cosmetic Chemists of Japan, vol. 24, No. 2, pp. 129-135, 1990.,(with English translation).

R. McMullen et al., "Optical Properties of hair: Effect of treatments on luster as quantified by image analysis", Journal of Cosmetic Science, vol. 54, pp. 335-351, 2003.

Japanese Office Action Issued Jul. 25, 2012 in Patent Application No. 2008-019502 (with English translation).

U.S. Appl. No. 13/388,866, filed Feb. 3, 2012, Nagase, et al.

\* cited by examiner

HAIR EVALUATION METHOD AND SYSTEM

TECHNICAL FIELD

The present invention relates to a method and a system for evaluating the appearance of hair objectively based on wave information on hair strands.

BACKGROUND ART

In general, when evaluating the change in physical ability and exercise ability of an aging person, there is a means to estimate about what age such person's ability corresponds to, by comparing with the average known ability corresponding to a certain age.

It is known that hairs become thinner, decrease in number, become gray, and become dry with age (Non-Patent Document 1). Techniques that have been proposed for evaluating hair properties include measuring and analyzing the physical properties of hair strands such as tensile strength and extension rate (Patent Document 1), and making a comprehensive evaluation of microscopic images of hair strands, taking measurements such as gloss and hue, evaluating scores of various questionnaires, and so on (Patent Document 2). There has been no simple technique, however, for evaluating the equivalent age of hair objectively.

[Non-Patent Document 1] C. R. Robbins, "Chemical and Physical Behavior of Human Hair," pp. 77-79, Springer-Verlag, New York, 2002

[Patent Document 1] JP-A-7-306200

[Patent Document 2] JP-A-2000-287953

DISCLOSURE OF THE INVENTION

Problem to be Solved by the Invention

In view of the foregoing conventional technologies, it is an object of the present invention to make it possible for anyone to make an objective evaluation of the appearance of hair by a simple technique without having to use a specialist's skills, and to allow evaluation of the appearance of hair in terms of determining the equivalent age.

Means for Solving the Problem

Figure 12:
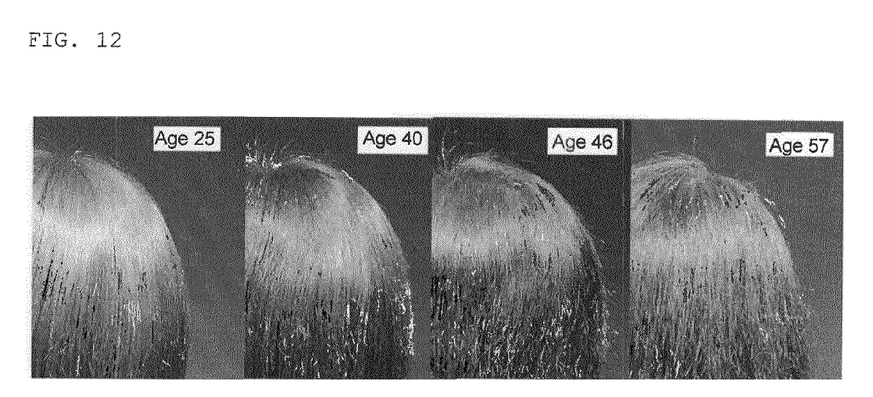
FIG. 12 is an image showing the backsides of heads of unpermed hair by age.

The inventors have achieved the present invention based on the following findings: (1) as shown in FIG. 12, the appearance of hair decreases in gloss with age, has less order of alignment of hair strands, and is more frizzy caused by the straying of hair strands from surrounding hair strands; (2) as for such changes in the appearance of hair with age, cosmetic specialists can evaluate the appearance of the entire length of the hair of the subject in terms of equivalent age from the gloss of the whole hair, the order of alignment of the hair strands, or the amount of frizziness of the hair strand based on their own experience, and the evaluations made by cosmetic specialists in terms of equivalent age are approximately consistent between the cosmetic specialists; (3) waves of unpermed hair strands are a dominant factor for any of the aging changes in the gloss of the entire length of the hair, the order of alignment of hair strands, and the amount of frizziness of hair strand; and (4) consequently, if a relationship between wave information of unpermed hair strands and appearance evaluations as to the gloss of hair, the order of alignment of hair strands, and the amount of frizziness of hair strand has been determined from a plurality of subjects in advance, then the relationship can be used to derive evaluations of the gloss, order, and frizziness of an arbitrary subject from the wave information in a quantitative manner.

More specifically, the present invention provides a hair evaluation method which includes: acquiring wave information on unpermed hair strands and an evaluation value of the appearance of hair from a plurality of subjects; determining a relation equation between the wave information and the evaluation value of the appearance; and evaluating the appearance of hair of an arbitrary subject from wave information on a hair strand of the arbitrary subject based on the relation equation.

For a system for carrying out this evaluation method, there is provided a hair evaluation system which includes:

means for storing a relation equation between wave information on unpermed hair strands and an evaluation value of appearance of hair;

means for inputting wave information on a hair strand of a subject; and arithmetic means for calculating an evaluation value of the appearance of whole hair of an arbitrary subject from the wave information on the hair strand of the arbitrary subject based on the relation equation.

Effect of the Invention

According to the present invention, it is possible to evaluate the appearance of hair of a subject in an objective manner easily by measuring the waves of hair strands of the subject.

The appearance of the hair to be evaluated may be gloss, order, and frizziness, which vary with age of the hair. Consequently, according to the present invention, the evaluations of the gloss, order, and frizziness of the hair made from the waves of hair strands can also be expressed in terms of equivalent age of the appearance of the hair, so that the subject can recognize the condition of his/her own hair easily.

EXPLANATION OF REFERENCE NUMERALS 1 hair evaluation system 2 main PC 3 keyboard
4 display
5 image scanner
6 digital camera
7 printer
8 communication line

BEST MODE FOR CARRYING OUT THE INVENTION

Hereinafter, the present invention will be described in detail with reference to the drawings.

As employed in the present invention, hair refers to human hair of the head, a hair strand refers to each single hair, and the whole hair refers to the whole of hair that forms a hairstyle.

The term "wave information on a hair strand" refers to a numerical measurement of the uniform or non-uniform wave shape which the outline of the hair strand has. The term "gloss of whole hair" refers to a numerical representation of the gloss that is determined by visual observation of the whole hair. The term "order" refers to a numerical representation of how ordered hair strands look in direction of the hair. The term "frizziness" refers to a numerical representation of how much the hair strand looks frizzy because of straying hair strands from the surrounding hair strands in the whole hair. These numerical representations may include logarithmic transformations if necessary.

The term "equivalent age" refers to the average of subject's ages that are empirically estimated by a plurality, preferably three or more, more preferably five or more, and even more preferably ten or more, of cosmetic specialists based on the appearance or property of hair strands or whole hair.

Figure 1:
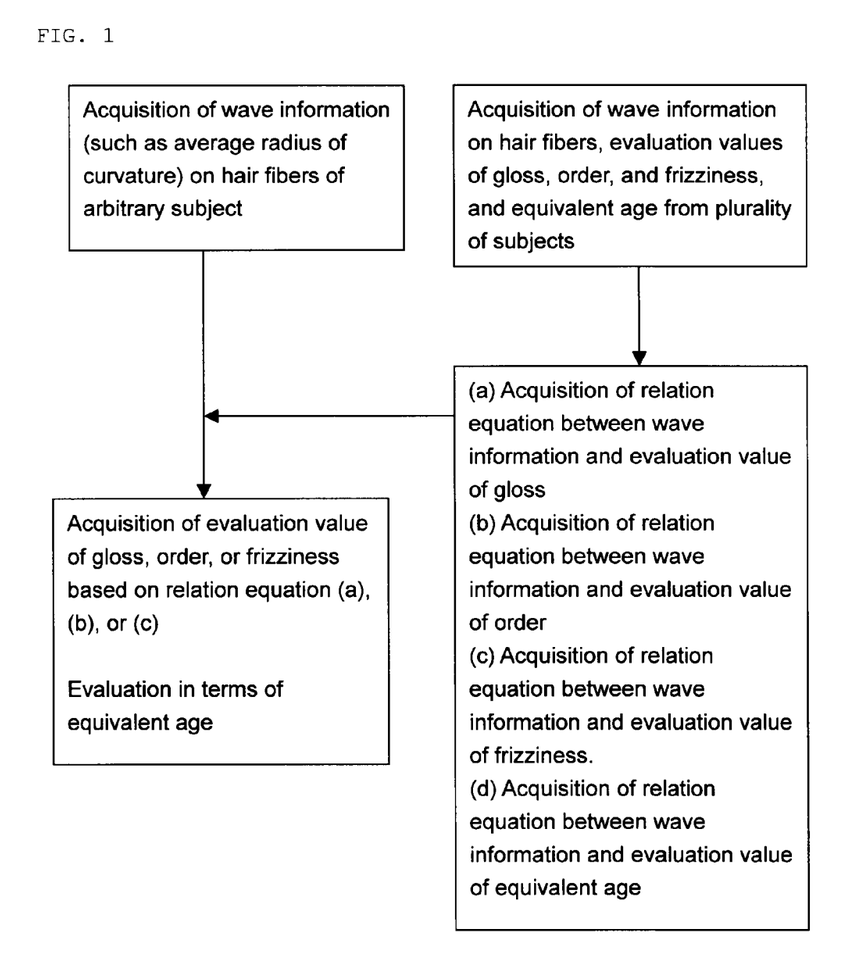
FIG. 1 is a flowchart of a hair evaluation method.
Figure 2:
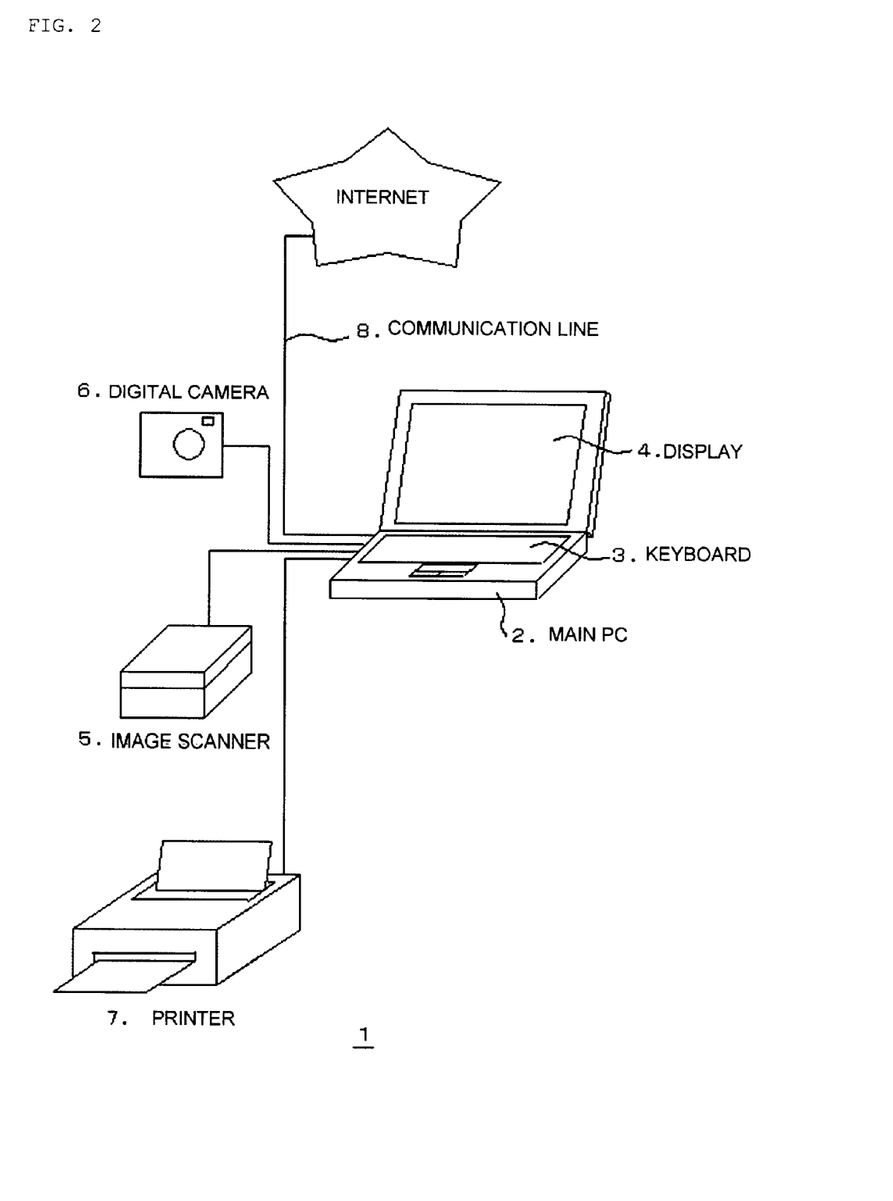
FIG. 2 is a block diagram of a hair evaluation system.

FIG. 1 is a flowchart of a hair evaluation method according to one example of the present invention. FIG. 2 is a block diagram showing one example of a hair evaluating system 1 for carrying out the evaluation method.

The hair evaluation system 1 includes: a main PC 2 which has predetermined arithmetic functions and serves as arithmetic means and storing means; and an accompanying keyboard 3 and display 4. The main PC 2 is connected with an image scanner 5, a digital camera 6, a printer 7, a communication line 8, and the like according to need, and is capable of communication over the Internet or the like.

As shown in FIG. 1, the hair evaluation method of the present invention includes calculating evaluation values of the gloss, order, and frizziness of whole hair of an arbitrary subject from wave information on hair strands of the subject by using predetermined relation equations.

The relation equations to be used here are regression formulae between the wave information and the evaluation values of the appearance of the whole hair. The regression formulae are determined from measurements of wave information on unpermed hair strands and evaluation values of appearance selected from among the gloss, order, and frizziness of the whole hair, the measurements and the evaluation values being acquired from a plurality of subjects, preferably 50 to 1000 subjects, in advance. Specifically, the relation equations may be a regression formula between measurements of wave information and evaluation values of gloss, a regression formula between measurements of wave information and evaluation values of order, a regression formula between measurements of wave information and evaluation values of frizziness, or a multivariate regression formula between measurements of wave information and evaluation values of gloss, order, and frizziness.

Figure 3:
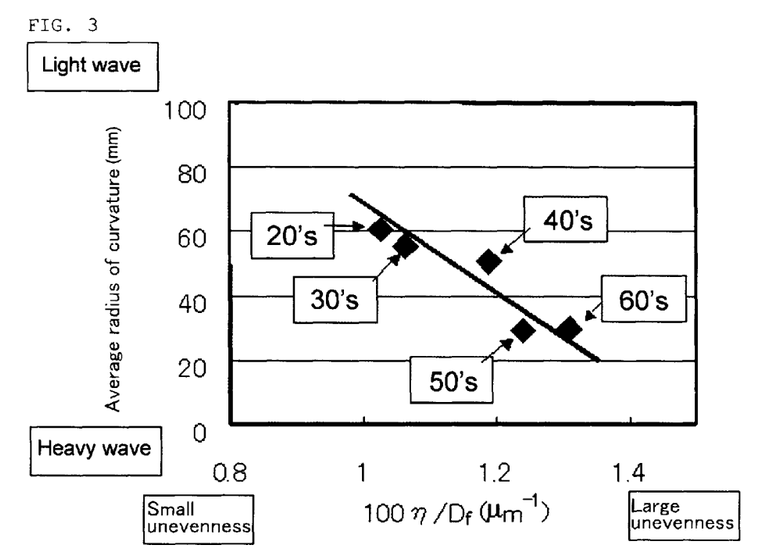
FIG. 3 is a chart showing the relationship between the distribution of ortho-cortical cells and para-cortical cells and the magnitude of waves of hair strands.

The foregoing is based on the findings of the inventors that measurements of the wave information and cosmetic specialists' evaluation values of gloss, order, and frizziness have a correlation therebetween, and that the waves of hair strands are a dominant factor responsible for the magnitudes of the gloss, order, and frizziness. As shown in FIG. 3, the inventors have made a study on the distribution of ortho-cortical cells and para-cortical cells in a cross section of a hair strand by using microbeam small angle X-ray scattering (see "Structural analysis of curly human hair strands by scanning microbeam SAXS" (see Journal of the Japanese Society for Synchrotron Radiation Research, Vol. 19 (No. 6), 371-377 (2006))). From the study, the inventors have found that: the lighter the wave of a hair strand is (i.e., the greater the radius of curvature is and the closer to straight the hair is), the more even the distribution of ortho-cortical cells and para-cortical cells is; and the heavier the wave of a hair strand is, the more uneven the distribution of ortho-cortical cells and para-cortical cells is. The inventors have also found that the unevenness of the distribution increases with age from twenties to sixties. This suggests that the age-based unevenness of the distribution of ortho-cortical cells and para-cortical cells produces waves of hair strands, confirming that the waves of the hair strands are a dominant factor responsible for aging changes of the appearance of the whole hair, including a decrease in gloss, a decrease in order, and an increase in frizziness.

As described in the foregoing document, the horizontal axis of FIG. 3 indicates the ratio q between average half-widths of peaks that are obtained from a scattering profile in azimuthal direction, including scattering peaks derived from intermediate filaments in the hair, on the convex side (P=0.2 to 0.4) and the concave side (P=0.6 to 0.8) of a curl, respectively, where P=0 is the position of the surface of the hair strand on the convex side of the curl and P=1 is the position of the surface on the concave side. The ratio η (=the average on the convex side of the curl/the average on the concave side of the curl) is normalized by the diameter $D_f$ of the hair strand and multiplied by 100.

The relation equations between the measurements of the wave information and the evaluation values of the appearance of the whole hair shall be derived by using unpermed hair strands. For a subject who has had hair permed but not in the most recent X years, hair strands in the range of Y=10×X (cm) from the roots can be safely handled as unpermed hair strands since hair grows at a rate of around 15 cm per year.

To uniformize the condition of hair strands of each subject, it is preferable to apply predetermined pretreatments like shampooing and towel drying, followed by unstyled natural drying.

In view of easy acquisition and data precision, the wave information on hair strands are preferably acquired by measuring 1 to 1000 hair strands, more preferably 3 to 500 hair strands, and even more preferably 5 to 250 hair strands per each subject. An average of the measurements is the wave information of that subject. When measuring hair strands, the hairs need not necessarily be pulled off or cut from the subject, depending on the measuring method. Specific examples of the method for measuring wave information include the following methods (1) to (7).

(1) Capture a hair strand image with an image scanner. Using image processing software, determine the radii of curvature on respective measuring points at predetermined intervals on the hair strand image captured. Average the measurements to obtain wave information. Here, the radii of curvature to be measured may have an upper limit. For example, a radius of curvature of 20 cm or greater may be assumed to be 20 cm. The number of measuring points on a single hair strand is preferably three or more.

(2) Place a transparent film showing concentric circles at a predetermined pitch (for example, 1 mm) in radius (radii of 1 mm to 200 mm) on a hair strand. Read the radii of curvature of the hair strand in a plurality of locations at predetermined intervals from the root of the hair strand (for example, four points at intervals of 1 cm), and determine the reciprocals (curvatures). A curvature smaller than 0.05 (in $cm^{-1}$) (when the radius of curvature is greater than 20 cm) may be approximated at 0.05. Average the curvatures at the plurality of locations. The reciprocal is the radius of curvature of the hair strand.

(3) Capture a hair strand image with an image scanner. With a plurality of reference curves having known average radii of curvature stored in image processing software, compare the hair strand image captured and the reference curves. Allow the known average radii of curvature of the best-matching reference curves to obtain wave information.

(4) Hang a hair strand at one end, and capture the shape with a three-dimensional image scanner. Using image processing software, determine the radii of curvature on respective measuring points at predetermined intervals on the hair strand image captured. Average the measurements to obtain wave information.

(5) Measure a hair strand for natural length (L0). Measure the hair strand for wave-straightened length (L) without stretching the hair itself. Calculate (L−L0)/L as the wave information. For length measurement, for example, the hair is initially fixed at one end with the other end hung free, and the distance from the fixed portion to the other end is measured (natural length L0). Next, the hair is straightened by hand without the hair itself being stretched out, and the length (L) between the ends is measured. A weight that is negligible in terms of stress (such as 0.1 to 0.01 g) may be hung on an end to measure the length (L) from the fixed portion to the weight. L0 and L may be measured with the root of the hair on either end.

(6) Hang a hair strand at one end, and photograph the shape with a digital camera. Measure the hair strand for how widely it horizontally spreads from a straight line that connects the one end and the other end of the hair strand, on measuring points at predetermined intervals on the straight line. Average the measurements to obtain wave information.

(7) Acquire in advance the relationship between the wave information that is obtained by any of the foregoing methods and measurements that are obtained by an optical gloss measuring method to be described later. The relationship is used to acquire wave information from a measurement acquired by the optical measuring method.

In each of the foregoing methods, the pieces of software necessary for calculating wave information may be installed in the main PC 2, so that the main PC 2 can calculate wave information on hair strands by using the image scanner 5 of the foregoing hair evaluation system 1 as the image scanner.

Now, when deriving the foregoing relation equations, the evaluation values of the gloss, order, and frizziness of the whole hair of a subject are preferably determined by keeping three- to ten-grade scores on the gloss, order, and frizziness according to respective predetermined criteria, preferably by three or more cosmetic specialists as raters, and averaging the scores of the raters. For example, the evaluation criteria for gloss, order, and frizziness may be as follows:

Gloss Criteria:
1 Not glossy,
2 Barely glossy,
3 Moderate,
4 Somewhat glossy, and
5 Glossy;

Order Criteria:
1 Well ordered hair strands,
2 Somewhat ordered hair strands,
3 Moderate,
4 Less ordered hair strands, and
5 Disordered hair strands; and Frizziness Criteria:
1 Not frizzy/Little straying,
2 Barely frizzy/Slight straying,
3 Moderate,
4 Somewhat frizzy/Certain straying, and
5 Frizzy/A lot of straying.

Examples of the optical methods for measuring hair gloss include the following methods (a) to (d):

(a) Using a gloss meter, measure a regular reflection intensity or a relative intensity of regular reflection with respect to diffuse reflection as a gloss index (JP-A-5-215681, JP-A-8-29258, etc.);

(b) Measure a reflection intensity while changing the angle of incidence of illuminating light to hair and the angle of acceptance of the same. Use the maximum reflection intensity (regular reflection intensity), a relative regular reflection intensity with respect to diffusion reflectance, or the half-width of each angle dependence profile of the regular reflection as a gloss index (Journal of Society of Cosmetic Chemists of Japan, Vol. 24, No. 2, (1990) pp. 129-135);

(c) Use a regular reflection intensity measured by a simplified gloss meter as a gloss index (JP-A-2000-206043, JP-A-2000-206044); and (d) Use the brightness of a regular reflection image of external light that is seen in a picture of the head including hair bundles or hair (highlight portion or so-called angel halo) as a gloss index (J. Cosmet. Sci., 54, 335-351 (2003)).

After the evaluation values of the gloss, order, and frizziness of the whole hair of each subject are acquired, the measurements of the foregoing wave information and the evaluation values of the gloss, order, and frizziness of the whole hair are subjected to a regression analysis. This determines relation equations between the wave information and the evaluation values of appearance of the whole hair selected from among the gloss, order, and frizziness, and the relation equations are stored in the main PC 2. This regression analysis may be performed by the main PC 2.

Moreover, a regression analysis may be performed on the actual ages of the subjects and the evaluation values of the gloss, order, and frizziness of the whole hair to determine relation equations therebetween. For example, the evaluation values on the gloss, order, and frizziness of the whole hair may be averaged by generations in steps of 10 years, and stored in the main PC 2 as equivalent-age evaluation values of the gloss, order, and frizziness in respective generations.

In the present invention, equivalent-age evaluation values may be acquired as overall appearance evaluations from the raters of the hair conditions. In such cases, the wave information and the equivalent-age evaluation values, or overall appearance evaluations, may be subjected to a regression analysis, and the relation equations therebetween may be stored in the main PC.

After the foregoing relation equations are stored in the main PC 2, wave information on hair strands of an arbitrary subject is acquired. The wave information is input to the main PC 2 to calculate the evaluation values of the appearance of the whole hair of the arbitrary subject based on the foregoing relation equations. As with the case of determining the foregoing relation equations, the hair strands of the arbitrary subject to acquire wave information from are unpermed hair strands. The whole hair need not necessarily be unpermed, however. It is only necessary that the area of the hair strands to acquire wave information is in an unpermed condition.

Here, the wave information on the hair strands of the subject shall be acquired by the same method as the measuring method that is used to acquire the foregoing relation equations between the wave information and the evaluation values of the appearance of the whole hair.

The means for inputting wave information to the main PC 2 may be the keyboard 3, the image scanner 5, the digital camera 6, or the like depending on the method of acquisition of the wave information. Alternatively, the main PC 2 may acquire images through the communication line 8 such as the Internet before the main PC 2 performs image processing to input wave information. Wave information may be input to the main PC 2 through the communication line 8 such as the Internet. In such cases, the communication line 8 will be referred to as inputting means.

From the input wave information of an arbitrary subject, the main PC 2 calculates and outputs evaluation values of appearance selected from among the gloss, order, and frizziness of the whole hair based on the foregoing relation equations. This makes it possible for the arbitrary subject to obtain evaluation values corresponding to the cosmetic specialists' evaluation values of gloss, order, and frizziness based on the wave information on his/her own hair strands without cosmetic specialists.

The main PC 2 may be equipped with a database that contains the correspondence between evaluation values of various types of whole hair and hair cosmetics and treatment methods, such as perm, suited to the respective evaluation values. Such a database may be retained in an external server so that the database can be accessed through the communication line 8. Based on evaluation values of appearance of the whole hair of a subject, the hair cosmetics or hair treatment methods corresponding to the evaluation values are then calculated and output automatically or under specific instructions. This makes it possible to use the hair evaluation system 1 as a hair care advice system that recommends hair treatment methods to customers in a barbershop, beauty parlor, face-to-face sales, recommendation sales using a communication line, or the like, or as a hair care advice system that allows ordinary persons to select hair cosmetics, hair treatment methods, and the like optimum to their own hair condition by themselves easily, according to the types of the hair cosmetics, the difficulty levels of the hair treatment methods, and the like stored as data.

If the main PC 2 memorizes equivalent-age evaluation values in advance, it may output which of the equivalent-age evaluation values the calculated evaluation values of an arbitrary subject correspond to. If the main PC 2 memorizes relation equations between wave information and equivalent-age evaluation values as overall appearance evaluations in advance, the subject can input his/her wave information to know equivalent age as overall appearance. As a result, it is possible for customers in a barbershop, beauty parlor, face-to-face sales, mail-, tele- or internet-order sales, and the like, and for ordinary persons who use the system by themselves to grasp the condition of their own whole hair more easily.

When the actual age of an arbitrary subject is input, relative difference information between equivalent age and the actual age may be output. Optimum hair cosmetics, hair treatment methods, and the like may be calculated and output in consideration of the relative difference information.

The output of the main PC 2, including the evaluation values of appearance selected from among the gloss, order, and frizziness, or the equivalent age, may be numerically displayed on the display 4 or the printer 7. The output may otherwise be displayed in terms of the position of an arbitrary subject in a chart showing the relationship between the wave information and the appearance evaluation values, or the position of the subject in the relationship chart accompanied with equivalent ages of the respective evaluation values, along with the hair image of the arbitrary subject and reference hair images if necessary. The output may be made displayable on other terminals through the communication line 8.

EXAMPLE

Example 1

(1) Acquisition of Relation Equations Between Hair Wave Information and Gloss, Order, and Frizziness For subjects, unpermed Japanese women (N=230) ages 10 to 70 were sampled at random. Each subject was given the pretreatment of shampooing and towel drying, followed by unstyled natural drying.

From each subject pretreated, ten hair strands were sampled from an upper side part of the head. An average radius of curvature of each hair strand was determined by the foregoing method (1) for measuring wave information. The radii of curvature of the ten hair strands of each subject were averaged further, and a logarithm thereof was determined as wave information.

The wave information obtained thus (the logarithm of the average radius of curvature: C) was classified into the following five groups depending on the value:

Group 1: $0.0 < C < 0.3 (N=15)$,

Group 2: $0.3 \leq C < 0.5 (N=67)$,

Group 3: $0.5 \leq C < 0.7 (N=111)$,

Group 4: $0.7 \leq C < 0.9 (N=30)$, and

Group 5: $0.9 \leq C (N=7)$.

Meanwhile, three raters consisting of cosmetologists or researchers engaged in the development of hair care products visually observed the head of each pretreated subject from behind to evaluate and give scores to gloss, order, and frizziness according to the following criteria. For each subject, the scores given by the raters in each of the gloss, order, and frizziness were averaged. The averages were the evaluation values of the gloss, order, and frizziness.

Each rater also made an evaluation of equivalent age as the overall appearance evaluation of the subject.

Gloss Criteria:
1 Not glossy,
2 Poorly glossy,
3 Moderate,
4 Somewhat glossy, and
5 Glossy.
Order Criteria:
1 Well ordered hair strands,
2 Somewhat ordered hair strands,
3 Moderate,
4 Less ordered hair strands, and
5 Disordered hair strands; and
Frizziness Criteria:
1 Not frizzy/Little straying,
2 Poorly frizzy/Slight straying,
3 Moderate,
4 Somewhat frizzy/Certain straying, and
5 Frizzy/A lot of straying.

Figure 4:
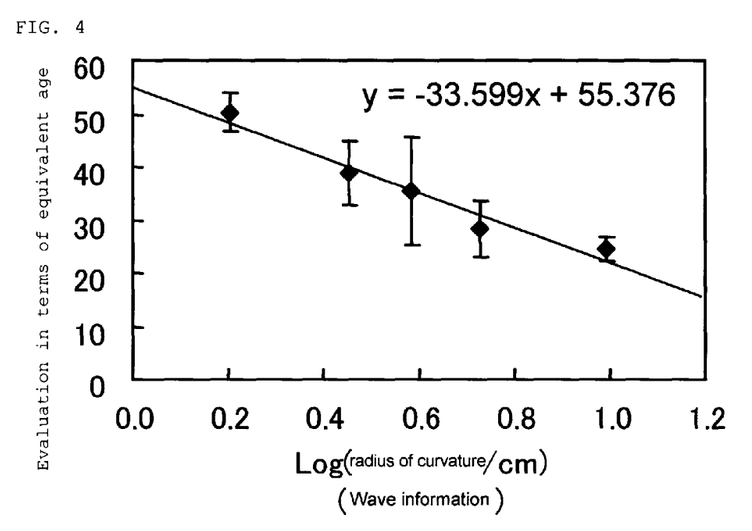
FIG. 4 is a chart showing the relationship between wave information and equivalent age in terms of overall appearance evaluation, in Example 1.
Figure 5:
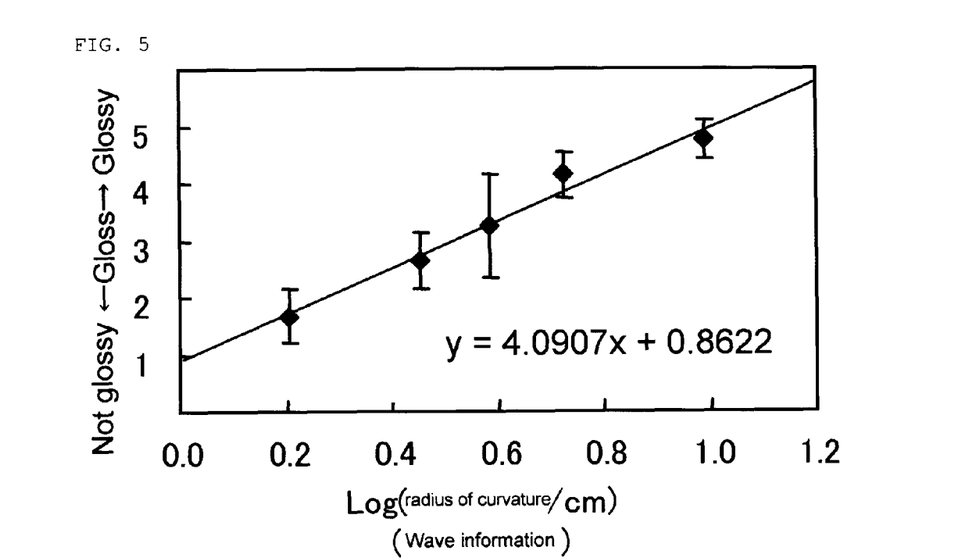
FIG. 5 is a chart showing the relationship between wave information and evaluation values of gloss in Example 1.
Figure 6:
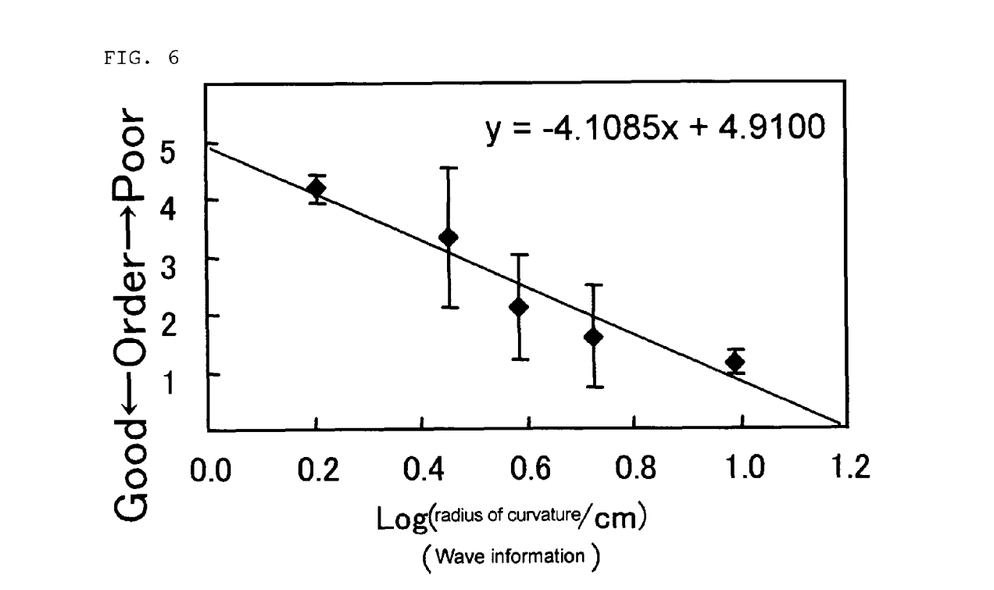
FIG. 6 is a chart showing the relationship between wave information and evaluation values of order in Example 1.

FIG. 4 shows the relationship between the groups of wave information and the equivalent ages or overall appearance evaluations ((equivalent age)=−33.599×(wave information)+ 55.376). The relationship between the groups of wave information and the evaluation values of gloss, the relationship between the groups of wave information and the evaluation values of order, and the relationship between the groups of wave information and the evaluation values of frizziness are each subjected to a regression analysis to determine the following relation equations:

FIG. 5 ((gloss)=4.0907×(wave information)+0.8622),

FIG. 6 ((order)=−4.1085×(wave information)+ 4.9100), and

Figure 7:
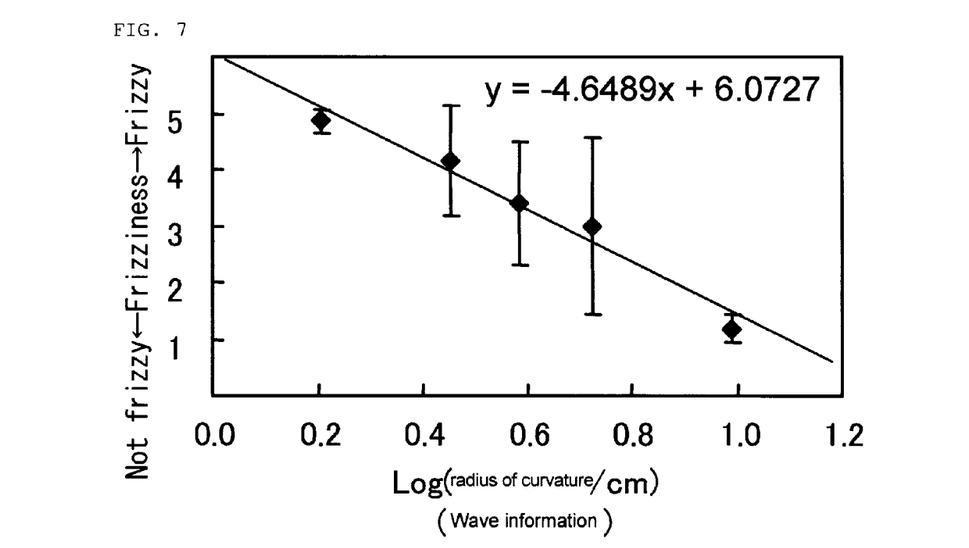
FIG. 7 is a chart showing the relationship between wave information and evaluation values of frizziness in Example 1.

FIG. 7 ((frizziness)=−4.6489×(wave information)+ 6.0727).

The evaluation values of the gloss, order, and frizziness of the whole hair were averaged by generations in steps of 10 years. Based on the averages, the following relation equations for converting the evaluation values of the gloss, order, and frizziness into equivalent age were determined:

The relation equation for converting gloss into equivalent age: (equivalent age)={(gloss)-7.5173}/ (−0.1193);

The relation equation for converting order into equivalent age: (equivalent age)={(order)+1.8129}/ 0.1209; and The relation equation for converting frizziness into equivalent age: (equivalent age)={(frizziness)+ 1.1806}/0.1268.

In FIG. 4, the wave information and the equivalent ages determined by the cosmetic specialists had a correlation therebetween. In FIGS. 5, 6, and 7, the wave information and the evaluation values of the gloss, the wave information and the evaluation values of the order, and the wave information and the evaluation values of the frizziness also had a correlation therebetween.

(2) Evaluations of Gloss, Order, and Frizziness from Wave Information on Arbitrary Subject With an unpermed Japanese woman age 28 as a subject, wave information on the subject was determined as in (1), and was found to be 0.89. From this wave information, evaluation values of equivalent age, gloss, order, and frizziness were determined based on the relation equations of FIGS. 4, 5, 6, and 7. The equivalent age determined directly from the wave information was age 25, the gloss was 4.5, the order was 1.3, and the frizziness were 1.9. The equivalent ages converted from the gloss, order, and frizziness were age 25, age 25, and age 25, respectively. The four equivalent ages were simply averaged to obtain age 25.

Meanwhile, the evaluation values of the equivalent age, gloss, order, and frizziness of the subject were acquired from three raters as in (1), and averages among the raters were calculated. The resulting evaluation values from the raters were age 24 in equivalent age, 5.0 in gloss, 1.0 in order, and 1.6 in frizziness, which were consistent with the evaluation values calculated from the wave information based on the foregoing relation equations.

Example 2

(1) Acquisition of Relation Equations Between Hair Wave Information and Gloss Index A total of 55 persons were extracted at random from among the subjects of Example 1 (230 persons), 5 to 10 persons from each of the 10-year generations. The subjects extracted were measured for gloss based on the foregoing method (d) for measuring gloss.

More specifically, two 100-W spotlights were used to illuminate the back of the head and hair of each subject from behind in directions of 45° above on the right and left of the subject, and the subject was photographed at a distance of 1 m from behind. The hair portion was clipped out of the photograph image by using image analysis software on the PC. On the clipped image, a high intensity area having a predetermined range of intensities from the maximum intensity was extracted as a regular reflection portion (highlight). An average intensity in this highlight portion was used as the gloss index of the hair.

Figure 8:
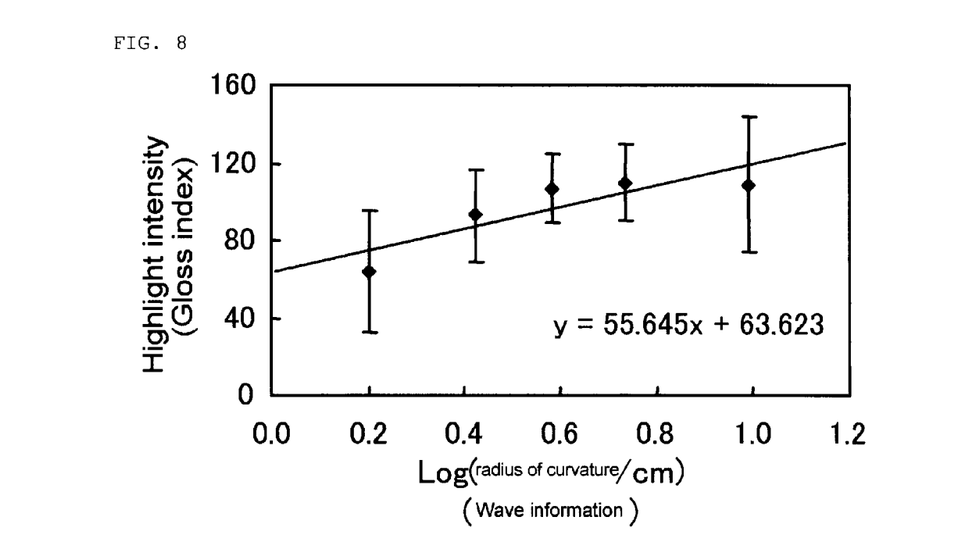
FIG. 8 is a chart showing the relationship between wave information and gloss indexes determined from photo images in Example 2.

As in Example 1, an average radius of curvature of the curls of ten hair strands was determined for each subject. The logarithm thereof was used as wave information. As in Example 1, the wave information was grouped in five grades according to the value of the wave information. FIG. 8 shows the relationship between the groups of information and the gloss index ((wave information)={(gloss index)-63.623}/ 55.645).

From FIG. 8, it can be seen that the wave information and the measurements of the gloss index have a correlation therebetween.

(2) Evaluations of Gloss, Order, and Frizziness from Wave Information Based on Gloss Index of Arbitrary Subject With the same unpermed Japanese woman age 28 as in Example 1 (2) as a subject, the gloss index of the subject was determined as in Example 2 (1), and was found to be 117. Wave information was determined from the measurement of the gloss index based on the relation equation of FIG. 8, and was found to be 0.96. From this wave information, evaluation values of equivalent age, gloss, order, and frizziness were also determined based on the relation equations of FIGS. 4, 5, 6, and 7. The equivalent age determined directly from the wave information was age 23, the gloss was 4.8, the order was 1.0, and the frizziness was 1.6. The equivalent ages converted from the gloss, order, and frizziness were age 23, age 23, and age 22, respectively. A simple average of the four equivalent ages was age 22.8, which was translated into age 25 in closest approximation in steps of 5 years.

As described in Example 1 (2), the evaluation values of the three raters on the equivalent age, gloss, order, and frizziness of this subject were age 24.0 in equivalent age, 5.0 in gloss, 1.0 in order, and 1.6 in frizziness. The evaluation values that were calculated from the wave information based on the gloss index of the present Example, according to the foregoing relation equations, were therefore consistent with the evaluation values of the raters.

Example 3

Hair Care Advice and Recommendation of Hair Treatment Method in Barbershop or Beauty Parlor A hair care advice system available for recommending a hair treatment method in a barbershop or beauty parlor was constructed from the hair evaluation system 1 shown in FIG. 2, using the main PC 2 that stored the relation equations acquired in Example 1 (1) for deriving the evaluation values of gloss, order, frizziness, and equivalent age from hair wave information, the method of regression analysis, and the correspondence between perm treatment methods and hair wave information in the form of computer software.

For example, this hair care advice system can be used in the following manner to present an appropriate hair treatment method in a barbershop or beauty parlor.

Initially, some ten hair strands are sampled from a customer. Wave information is acquired by using the image scanner as in Example 1 (1), and taken into the main PC 2.

For example, if this customer has wave information of 0.16, a regression analysis performed by using regression analysis software built in the main PC 2 produces evaluation values of age 50 in equivalent age, 1.5 in gloss, 4.3 in order, and 5.3 in frizziness.

These evaluations are printed as a chart and presented to the customer. For reference purpose, the chart may show the average values of the data on the 230 persons investigated for determining the relation equations in Example 1 (1).

Figure 9:
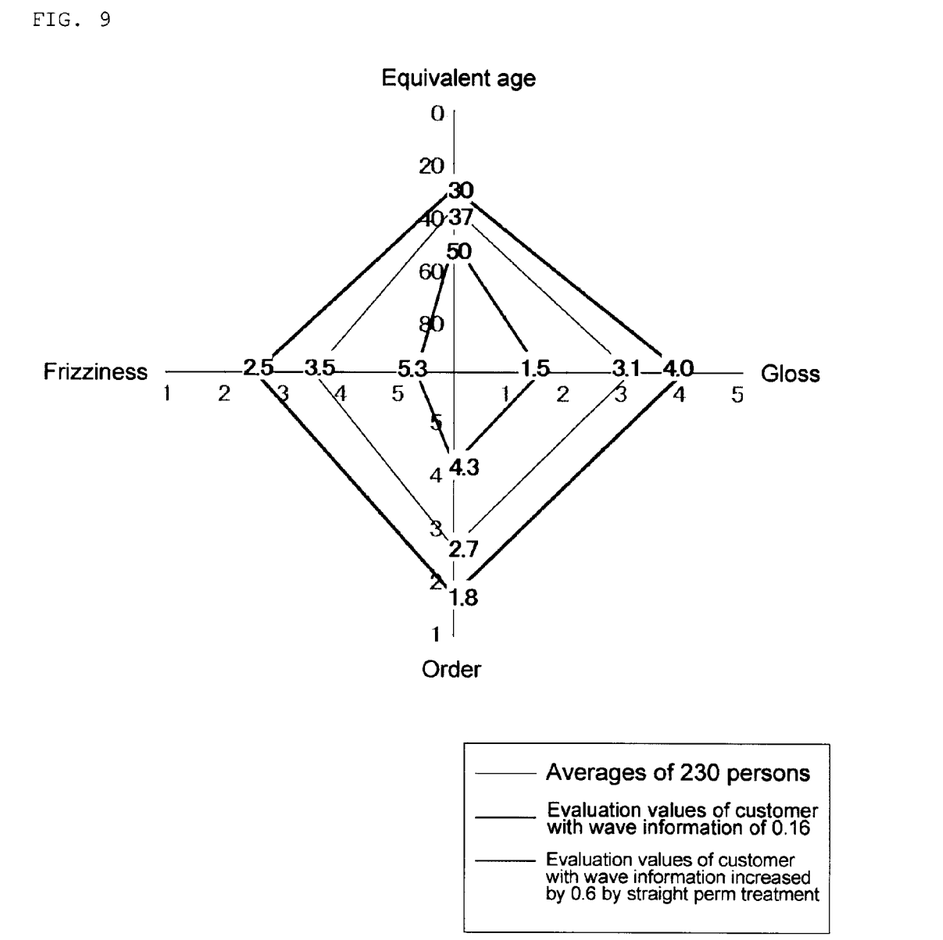
FIG. 9 is a chart showing evaluation values of equivalent age, gloss, order, and frizziness in Example 3.

Based on the correspondence between the perm treatments and the hair wave information according to the computer software built in the main PC 2, an improvement to the hair waves is presented for situations when a predetermined straight perm treatment is applied. For the customer having the foregoing wave information of 0.16, an increase of 0.6 to the wave information results in evaluation values of age 30 in equivalent age, 4.0 in gloss, 1.8 in order, and 2.5 in frizziness. The changes are shown in color on the same chart, and presented to the customer. FIG. 9 shows the chart. The customer can thus recognize the effect of the straight perm treatment easily.

It will be appreciated that it is also possible to acquire the wave information from customer's hair and present the current evaluation values and estimated evaluation values after hair treatment to the customer even when the type of the hair treatment, the agents to be used for the hair treatment, the treatment time, the treatment temperature, and the like are changed. With the present system, it is therefore possible for the customer to understand the effects of various hair treatments easily, and for the barbershop or beauty parlor to recommend various hair treatments easily.

Example 4

Hair Care Advice and Sales Recommendation of Hair Cosmetics in Face-to-Face Sales A hair care advice system available for face-to-face sales of hair cosmetics in a sales outlet was constructed from the hair evaluation system 1 shown in FIG. 2, using the main PC 2 that stored the relation equations acquired in Example 2 (1) for deriving the evaluation values of gloss, order, frizziness, and equivalent age from hair wave information, the method of regression analysis, the method of image analysis for calculating the gloss index from a hair image, and the correspondence between hair cosmetics and hair wave information in the form of computer software.

For example, this hair care advice system can be used in the following manner to present an appropriate hair cosmetic in face-to-face sales.

Initially, the head and hair of a customer is photographed with a digital camera under the same condition as in Example 2 (1). The image data is captured into the main PC 2, and an image analysis is performed by image analysis software built in the main PC 2 to acquire the gloss index of the customer's hair.

Suppose, for example, that the customer has a gloss index of 70. With the gloss index as an input value, a regression analysis is performed to obtain wave information of 0.11 by regression analysis software that is built in the main PC 2 and based on the relation equation of FIG. 8. A regression analysis is also performed as in Example 3 by using the regression analysis software built in the main PC 2 to produce evaluation values of age 52 in equivalent age, 1.3 in gloss, 4.4 in order, and 5.5 in frizziness.

These evaluations are displayed as a chart on the display and presented to the customer. The chart may be printed out by the printer 7 and handed to the customer. For reference purpose, the chart may also show the average values of the data on the 230 persons as in Example 3.

Suppose that a hair cosmetic A that is known to relax hair waves gradually in continuous use, with an increase of 0.3 to the wave information, is applied to this customer. The resulting evaluation values of the customer's hair strands will be age 41 in equivalent age, 2.6 in gloss, 3.2 in order, and 4.1 in frizziness, based on the correspondence between the hair cosmetic and the hair wave information according to the computer software built in the main PC 2.

When using a straight perm solution B that relaxes hair waves with an increase of 0.6 to the wave information, the resulting evaluation values will be age 31 in equivalent age, 3.8 in gloss, 2.0 in order, and 2.8 in frizziness.

Figure 10:
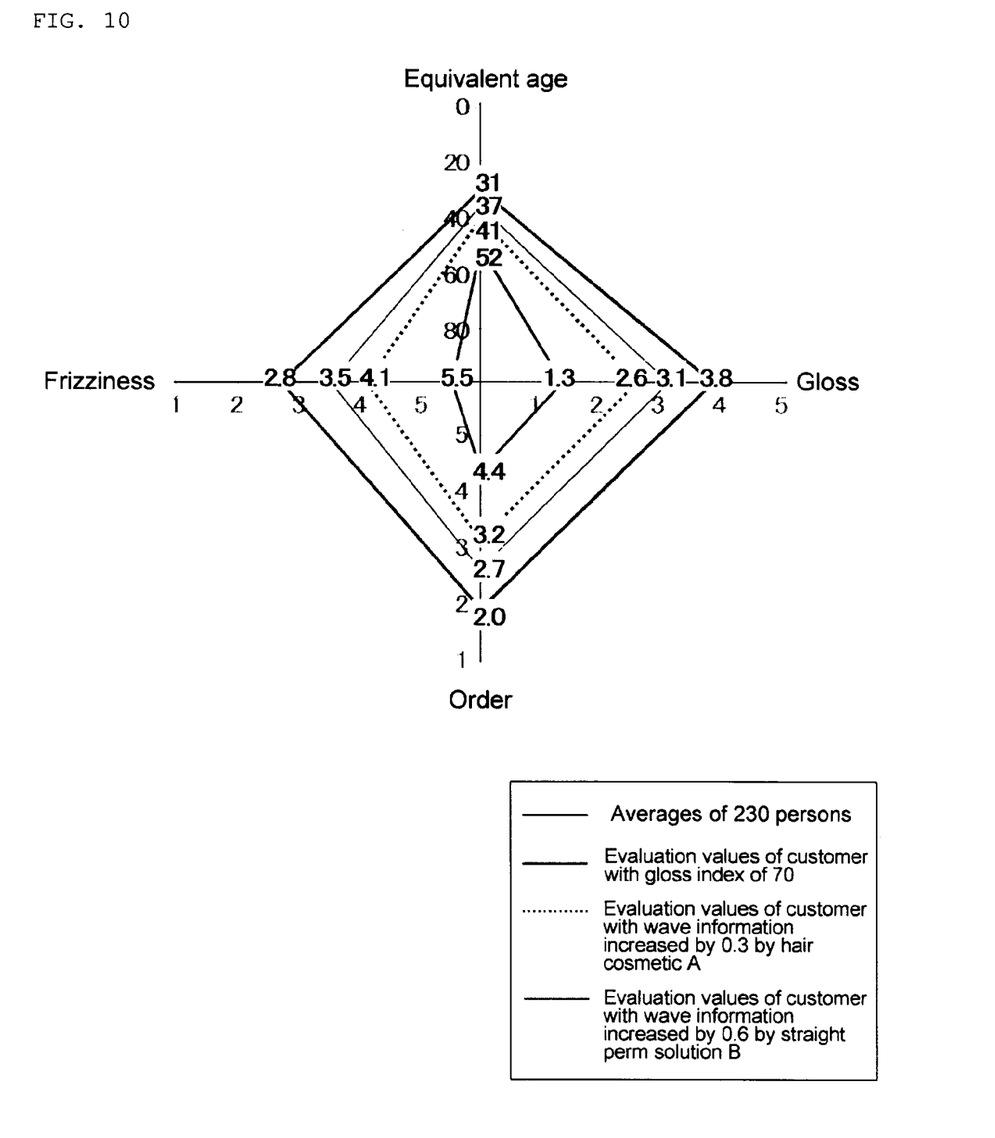
FIG. 10 is a chart showing evaluation values of equivalent age, gloss, order, and frizziness in Example 4.

The changes are shown in different color on the same chart, and presented to the customer. FIG. 10 shows the chart. The customer can thus recognize the characteristics and differences of the hair cosmetic A and the straight perm solution B easily. The seller can present the effects of various hair cosmetics to the customer similarly and recommend hair cosmetics suited to customer demands easily.

Example 5

Hair Care Advice and Sales Recommendation of Hair Cosmetics Over Internet

A hair care advice system available for recommendation sales of hair cosmetics through a communication line was constructed from the hair evaluation system 1 shown in FIG. 2, using the main PC 2 that stored the relation equations acquired in Example 2 (1) for deriving the evaluation values of gloss, order, frizziness, and equivalent age from hair wave information, the method of regression analysis, image analysis for calculating the gloss index from a hair image, and the correspondence between hair cosmetics and hair wave information in the form of computer software. This hair care advice system can receive image data from a customer's PC or cellular phone and transmit the result of analysis through the communication line.

For example, the hair care advice system can be used in the following manner to present an appropriate hair cosmetic to a customer through the communication line.

Initially, the customer transmits a digital photograph of his/her own or other's head and hair to the hair care advice system through the communication line. The hair care advice system performs an image analysis on the received digital photograph of the hair of the head by using image analysis software built in the main PC 2, thereby acquiring the gloss index of the hair. The hair care advice system also performs a regression analysis by using regression analysis software that is built in the main PC 2 and based on the relation equation of FIG. 8, and thereby acquires wave information of 0.26 from a gloss index of 78, for example. The hair care advice system also performs a regression analysis as in Example 3 by using the regression analysis software built in the main PC 2, and thereby acquires evaluation values of age 47 in equivalent age, 1.9 in gloss, 3.8 in order, and 4.9 in frizziness.

These evaluations are rendered as a chart and transmitted to the customer through the communication line. For reference purpose, the chart may also show the averages values of the data on the 230 persons as in Example 3.

Figure 11:
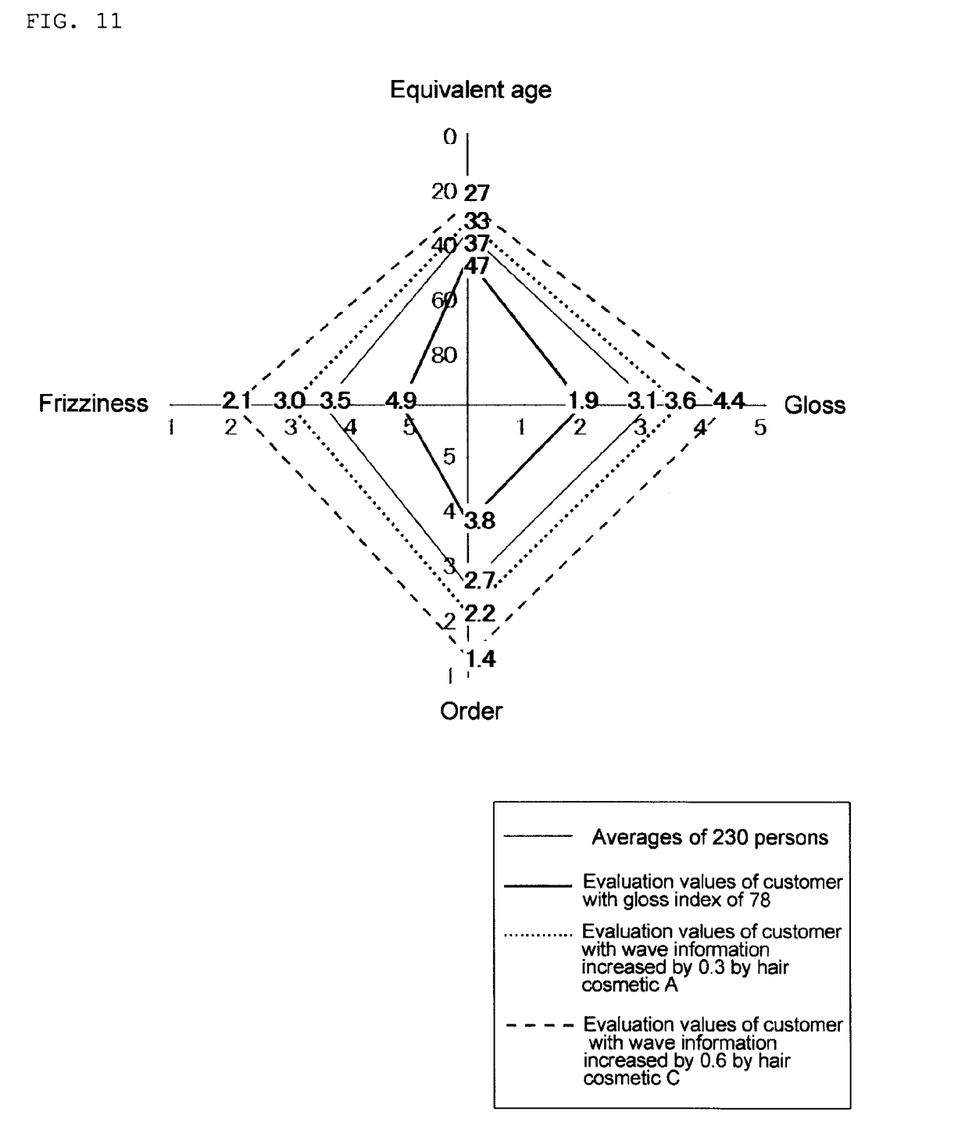
FIG. 11 is a chart showing evaluation values of equivalent age, gloss, order, and frizziness in Example 5.

A list of a plurality of hair cosmetics that are known to be capable of relaxing hair waves is presented to the customer through the communication line. The customer selects one or more hair cosmetics (for example, hair cosmetics A and C) from the list, and transmits the selection information. Changes resulting from the use of the hair cosmetics selected by the customer are shown in different colors on the same chart for transmission. FIG. 11 shows the chart.

This makes it possible for the customer to use the hair care advice system when desired without personally going to sales outlets. The seller can also present the characteristics or differences of various hair cosmetics to the customer in an untended manner through the cooperation of the pieces of software built in the main PC 2.

Industrial Applicability

The hair evaluation method and the hair evaluation system of the present invention are useful for such occasions as developing hair care products, and giving hair care advice and recommending optimum hair cosmetics or hair treatment methods such as perm in face-to-face sales over the counter or in recommendation sales through a communication line.

The invention claimed is:

1. A hair evaluation method comprising: acquiring wave information on unpermed hair strands and an evaluation value of the appearance of hair from a plurality of subjects; determining a relation equation between the wave information and the evaluation value of the appearance; and evaluating the appearance of whole hair of an arbitrary subject from wave information on a hair strand of the arbitrary subject based on the relation equation, wherein the evaluation value of the appearance is at least one evaluation value selected from the group consisting of gloss of the whole hair, order of alignment of the hair strand, and frizziness of the hair strand.

2. The hair evaluation method according to claim 1, wherein a logarithm of an average radius of curvature of the hair strand is used as the wave information.

3. A hair evaluation system comprising:
means for storing a relation equation between wave information on unpermed hair strands and an evaluation value of appearance of whole hair;
means for inputting wave information on a hair strand of an arbitrary subject; and
arithmetic means for calculating an evaluation value of the appearance of whole hair of the arbitrary subject from the wave information on the hair strand of the arbitrary subject based on the relation equation, wherein the evaluation value of the appearance is at least one evaluation value selected from the group consisting of gloss of the whole hair, order of alignment of the hair strand, and frizziness of the hair strand.

4. The hair evaluation system according to claim 3, further comprising means for measuring the wave information based on an image of the hair strand.

5. The hair evaluation system according to claim 3, further comprising: a database containing correspondence between evaluation values of various types of whole hair and hair cosmetics or hair treatment methods suited to the respective evaluation values; and means for selecting at least one hair cosmetic or at least one hair treatment method suited to an arbitrary subject based on an evaluation value of the appearance of whole hair of the arbitrary subject.

6. A method for evaluation of hair in an arbitrary subject, the method comprising:
acquiring wave information on unpermed hair strands and an evaluation value of equivalent age;
determining a relation equation between the wave information and the equivalent age; and
evaluating the equivalent age of whole hair of an arbitrary subject from wave information on a hair strand of the arbitrary subject based on the relation equation, wherein the evaluation value of the appearance is at least one evaluation value selected from the group consisting of gloss of the whole hair, order of alignment of the hair strand, and frizziness of the hair strand.

* * * * *